United States Patent
Sarin et al.

(10) Patent No.: US 6,184,429 B1
(45) Date of Patent: Feb. 6, 2001

(54) OLIGOMERIZATION OF ALPHA-OLEFINS

(75) Inventors: Rakesh Sarin, Faridabad; Sabyasachi Sinha Ray, New Delhi; Deepak Kumar Tuli, Faridabad; Madan Mohan Rai, Faridabad; Sobhan Ghosh, Faridabad; Akhilesh Kumar Bhatnagar, Faridabad, all of (IN)

(73) Assignee: The Indian Oil Corporation Ltd., Mumbai (IN)

( * ) Notice: Under 35 U.S.C. 154(b), the term of this patent shall be extended for 0 days.

(21) Appl. No.: 09/354,844

(22) Filed: Jul. 16, 1999

Related U.S. Application Data

(62) Division of application No. 08/972,951, filed on Nov. 19, 1997, now Pat. No. 5,922,636.

(51) Int. Cl.$^7$ ..................................................... C07C 2/02
(52) U.S. Cl. ........................ 585/524; 585/520; 585/521; 585/523
(58) Field of Search ..................................... 585/511, 512, 585/520, 521, 523, 524; 502/164, 150, 156, 170, 174

(56) References Cited

U.S. PATENT DOCUMENTS

| | | | |
|---|---|---|---|
| 3,637,503 | 1/1972 | Giannetti et al. | 585/10 |
| 4,031,159 | 6/1977 | Mandai et al. | 585/532 |
| 4,107,080 | 8/1978 | Taniyasu et al. | 502/169 |
| 4,167,534 | 9/1979 | Petrillo et al. | 585/18 |
| 4,219,691 | 8/1980 | Mandai et al. | 585/532 |
| 4,268,418 | 5/1981 | Hoff | 502/169 |
| 4,363,746 | 12/1982 | Capshew | 502/107 |
| 4,400,565 | 8/1983 | Darden et al. | 585/10 |
| 4,504,637 | 3/1985 | Shiga et al. | 526/119 |
| 4,629,714 | 12/1986 | Shelly | 502/113 |
| 5,068,487 | 11/1991 | Theriot | 585/510 |
| 5,136,118 | 8/1992 | Buchanan | 585/255 |
| 5,191,140 | 3/1993 | Akatsu et al. | 585/525 |
| 5,196,635 | 3/1993 | Kumar et al. | 585/532 |
| 5,922,636 | * 7/1999 | Sarin et al. | 502/169 |

* cited by examiner

*Primary Examiner*—Benjamin L. Utech
*Assistant Examiner*—Thuan D. Dang
(74) *Attorney, Agent, or Firm*—Venable; George H. Spencer; Ashley J. Wells

(57) ABSTRACT

This invention relates to a catalyst composition capable of effecting selective oligomerisation of olefins contained in cracked refinery distillate streams, comprising of olefins, aromatics, paraffins and cycloparaffins. The catalyst composition gives very high conversion of olefins to poly olefins, which after distillation and stabilization by hydrogenation affords lubricating oil base stocks. The catalyst composition comprises of an aluminum halide and a transition metal alkoxide belonging to group IVB.

6 Claims, No Drawings

OLIGOMERIZATION OF ALPHA-OLEFINS

CROSS-REFERENCE TO RELATED APPLICATION

This Application is a divisional of U.S. Application Ser. No. 08/972,951 filed Nov. 19, 1997, now U.S. Pat. No. 5,922,636 issued Jul. 13, 1999.

This invention relates generally to a novel catalyst composition, comprising of an aluminum halide and a metal alkoxide belonging to group IVB, for selectively oligomerising olefins, present in a mixture of olefins, aromatics, paraffins and cycloparaffins, to polyolefins in good yields. A particular application of invention is particularly useful for oligomerisation of olefins, contained in cracked refinery distillate streams to give poly olefins, which after the steps of distillation and stabilization by hydrogenation, give oligomers suitable for use as lubricating oil base stocks.

BACKGROUND OF THE INVENTION

Synthetic oil base stocks having viscosities of about 4 to 30 cSt or above at 100° C. have been prepared in prior art by oligomerisation of olefins by conventional or modified Friedel-Craft catalysts. Thus by contacting the alphaolefins with boron trifluoride containing various promoters, synthetic oils suitable for lubricant use have been prepared, such as described in U.S. Pat. Nos. 4,400,565; 5,068,487 and 5,191,140. However, boron trifluoride being pulmonary irritant is fast being replaced by less hazardous catalysts like aluminum halides.

A number of aluminum halide catalyst systems have been disclosed for oligomerisation of alpha olefins to poly alpha olefins which could be used as lubricating oil base stocks possessing low pour points, higher viscosity index and good oxidation stability. U.S. Pat. No. 3,637,503 discloses the oligomerisation of alpha olefins having from 4 to 16 carbon atoms in the presence of aluminum chloride and a non-polymerizing hydrocarbon diluent. Similarly aluminum chloride alone or along with organic promoters have been used to oligomerise alpha olefins either pure or in presence of a non-oligomerising hydrocarbon diluent. See for example U.S. Pat. Nos. 5,196,635; 5,136,118; 4,107,080; 4,219,691 and 4,031,159. It is also known in the related field the possibility of oligomerising olefins in which the double bond is statistically distributed along the entire carbon chains. Thus U.S. Pat. No. 4,167,534 discloses tile oligomerisation of olefins obtained from a PACOL-OLEX process, by contacting with aluminum chloride to obtain oligomers which after distillation and catalytic hydrogenation gave the lubricating oil. Even though the feed stock for oligomerisation was predominantly olefinic (up to 95%), the yield and the viscosity of the resulting oligomer were very poor.

However, all these processes pertain to oligomerisation of either pure or mixtures of pure alpha-olefins, and suprisingly there are no reports on the utilisation of linear olefins contained in refinery streams, for the production of synthetic lubricant base stocks. Various refinery produced cracked distillate streams, particularly from Coker and FCC units, are quite rich in desired alpha-olefins, which can be selectively concentrated by the process of urea adduction.

A major deficiency with the conventional Friedel-Craft catalysts is their inability to selectively oligomerise olefins in the presence of other unsaturated compounds like aromatics. However, aluminum chloride alone or with promoters is known to promote the alkylation of aromatics with olefins, when applied to cracked refinery distillate streams which contained appreciable amounts of aromatics along with olefins. The oligomeric product thus obtained contain alkylated aromatics, which made these products unsuitable for use as lubricating oils, because of very poor oxidation stability. No prior art method either discloses or teaches any catalyst system which can selectively oligomerise olefins to poly olefins in the presence of aromatics. Consequently, it is infact impossible to prepare an olefin oligomer having high viscosity index and high oxidation stability which could be qualified for such uses as gas turbine oil, hydraulic fluid for air crafts, crankcase oils, etc by selective oligomerisation of olefins present in the cracked refinery stream distillates which also contain aromatics, besides paraffins and cycloparaffins, by use of Friedel-Craft catalyst systems disclosed in the prior art. The present invention provides for a catalyst composition for preparation of olefin oligomers suitable for use as lubricating oils by selective oligomerisation of olefins, contained in cracked refinery stream distillates, which have been processed through a step of urea adduction.

OBJECTS OF THE INVENTION

An object of the present invention is to propose a catalyst composition for selectively oligomerising olefins present in cracked refinery stream distillates which comprised of olefins, aromatics, paraffins and cycloparaffins having 8 to 20 carbon atoms.

A further object of this invention is to propose a catalyst composition which provides higher conversion of olefins present in the cracked refinery stream distillates, processed through a step of urea adduction and containing upto 5% aromatics.

Yet another object of the present invention is to propose a catalyst system for selective oligomerisation of olefins contained in refinery distillate streams to produce oligomers having high viscosity index, low pour point and higher oxidation stability for their use as base stocks in synthetic lubricants.

DESCRIPTION OF THE INVENTION

According to this invention, there is provided a catalyst composition for use in oligomerisation of olefins, contained in refinery distillate streams, comprising an aluminum halide component and a catalyst component selected from an alkoxide of a metal belonging to group IVB.

Further according to this invention, there is provided a process for preparing polyalphaolefin synthetic lubricants, comprising in oligomerisation of olefins of cracked refinery streams, having 8 to 20 carbon atoms, in the presence of corresponding paraffins, naphthenes and aromatics, in the presence of a catalyst consisting of an aluminum halide and group IVB transition metal alkoxide, to provide an olefin oligomer, having viscosity of 7–30 cSt at 100° C.

The catalyst composition used in the oligomerisation process of the present invention is a two component system comprising (A) an aluminum halide component and (B) a second catalyst component which is a alkoxide of a metal belonging to group IVB. The aluminum halides which are suitable for use in the catalyst system of the present invention include aluminum fluoride, aluminum chloride, aluminum bromide and aluminum iodide and mixture thereof. The preferred aluminum halide is aluminum chloride. The second component of the proposed oligomerisation catalyst system comprises a metal alkoxide having the general formula $M(OR)_4$ wherein M is selected from the group of metals belonging to group IV B of the periodic table and R is alkyl of 1 to 12 carbon atoms or alkylaryl having alkyl chain of 1–12 carbon atoms. Preferably R is lower alkyl of 2 to 6 carbon atoms.

A preferred catalyst composition is obtained when metal alkoxide is a titanium alkoxide. A particularity preferred catalyst composition contains aluminum chloride and a titanium alkoxide such as titanium tetra isopropoxide or titanium tetra n-butoxide.

The molar ratio of aluminum halide to the transition metal alkoxide is important for optimum catalyst activity and for product quality in terms of viscosity and pour points. Generally the molar ratio of aluminum to transition metal is from 100:1 to 4:1, preferably about 60:1 to 10:1. The amount of aluminum halide catalyst can vary and amounts of from about 0.5 to 10 weight percent based on the amount of olefin is preferred. The specially preferred amount of aluminum halide is from 1 to 4 weight percent of olefins.

The raw material suitable for the present catalyst composition can consist of alpha olefins having number of carbon atoms between 8 and 24, n-olefins having the double bond statistically distributed along the entire carbon chain and having number of carbon atoms between 8 and 24, and the mixtures of n-olefins and alpha olefins in any ratio. The proposed catalyst composition is also suitable for raw materials obtained from PACOL process or from wax cracking and containing a mixture of olefins and paraffins and having number of carbon atoms between 8 and 24. Yet another raw material suitable for the present catalyst composition is the cracked refinery distillate cuts i.e. distillate cuts from FCC or coker units. These cuts were mixtures of olefins, aromatics, paraffins and cycloparaffins having number of carbon atoms between 8 and 24.

A preferred feed for oligomerisation with the catalyst composition of the present invention is as obtained through the process of urea adduction, of cracked refinery distillate streams. Methods are generally known in the prior art to obtain linear olefins and linear paraffins mixtures, by urea adduction of cracked refinery distillate streams, viz., naphtha, kerosene, diesel and gas oil. See, for example, A. Hoope, in "Advances in Petroleum Chemistry and Refining", Vol. 8, Ed., Kobe-McKetta, Inter-Science Publication, New York, 1964, which is incorporated by reference. However the urea adducted olefin rich feed is generally contaminated with 0.1–5.0% aromatics, depending upon the process conditions. Surprisingly, it was found that the catalyst composition of the present invention results in selective oligomerisation of olefins contained in the cracked refinery distillate streams, processed through the step of urea adduction.

The olefins arc oligomerised in contact with the present catalyst composition under conventional oligomerisation conditions. Oligomerisation is conducted at temperatures ranging from 30–200° C., preferentially from about 70 to 120° C. The reactions can either be conducted under reflux conditions or in a autoclave under autogeneous pressure. For effecting the oligomerisation of olefins by the catalyst composition of the present invention, the appropriate amount of aluminum halide and transition metal alkoxide are premixed in the presence of a inert non-polymerizing solvent (i.e. n-heptane, n-octane etc.) and the resulting mixture added slowly to the olefinic feed stock. However, no difference was observed even by dissolving the transition metal alkoxide in the olefinic feed stock and subsequent stepwise addition of aluminum halide to this mixture or vice versa. Lower reaction temperatures were generally associated with enhancement in the viscosity of the oligomer and a decrease in the overall yield. The readction is normally carried out over a period of about 1 to 12 hours, preferably for about 1 to 4 hours.

The regulation of the molecular weight of the oligomers produced and hence other physical characteristics like viscosity, viscosity index and pour point, can be controlled during the oligomerisation by changing the ratio of aluminum halide to metal alkoxide, by variation in reaction temperature and by variation in reaction duration. After completing the oligomerisation reaction, the product is passed through a column of silica/alumina to remove the residual catalyst, and then subjected to distillation under reduced pressure to remove unoligomerised products and olefin dimers. To further improve the oxidation stability and/or thermal stability of the product, it can be subjected to hydrogenation treatment by use of typical hydrogenation catalysts such as Raney nickel, nickel on Kieselguhr or by Pd on charcoal. At present, the reaction mechanism of the complex of aluminum halide with transition metal alkoxide which is responsible for the selective oligomerisation of olefins in the presence of other unsaturated compounds like aromatics is yet to be clarified. However, it is likely that oligomer chain growth occurs as a result of olefin co-ordination on transition metal which has unoccupied co-ordination sites. Subsequently, olefin insertion can take place into a transition metal carbon bond to give oligomeric chain growth. However, the bulky aromatics are not able to make transition metal—carbon bonds and hence and excluded in the chain growth step. Finally the chain transfer can occur as a result of $\beta$-hydrogen elimination from the oligomeric chain attached to the transition metal and the catalytic center, namely, transition metal—carbon bond is restored again.

As will be understood from the fore-going elucidation, according to the oligomerisation catalyst composition of the present invention it is possible to selectively oligomerise olefins in the presence of aromatics, to get the oligomer oil. These oligomers can be tailor made to a viscosity range of 7 to 30 cSt at 100° C. by variation effected in the catalyst composition and by process parameters. After stabilization by hydrogenation these oligomers show high viscosity index, low pour points, excellent thermal/oxidation stability and can be used as synthetic lubricant base stock.

The present invention will be further illustrated by, but by no means is limited to, the following examples. In the following examples, the kinematic viscosity was determined in the manner described in ASTM-D-45, the viscosity index was determined in the manner described in ASTM-D-2270 and the pour point was determined in the manner described in ASTM-D-97. The detection of aromatics in the feed stock and oligomeric oil was carried out by NMR spectroscopy.

EXAMPLE-1

The reaction was carried out in a 1 litre four necked round bottom flask, fitted with a mechanical stirrer, a solid addition funnel, a thermometer and a gas purging tube. The system was kept under a positive pressure of dry nitrogen and 2% of anhydrous aluminum chloride and 0.2% titanium isopropoxide was added. Keeping Al/Ti ratio equal to 21, 500 g of 1-decene was dropwise added to the mixture over a period of 1 hour. The temperature of this stirred mixture was raised to 100° C. and oligomerisation was carried out for a period of 2 hours. After completion of reaction, the product mixture was filtered through a bed of silica to remove the deactivated catalyst. The filtrate was subjected to flushing at 160° C./0.5 mm Hg to remove unreacted decene and its dimers, to obtain the oligomerised oil. The performance evaluation of products obtained is described in Tables 1 & 2.

EXAMPLE-2

In a experimental set up similar to the one as described for example-1, 2% aluminum chloride and 0.05% Ti(Obu)$_4$ was mixed together and reacted with 1-decene. The oligomerisation reaction was carried out at 80/100° C. and oligomeric product was isolated as described in example-1. The results are reported in Table-1 & 2.

EXAMPLE-3

The reaction was carried out as described for example 1, and using the identical catalyst composition, except that the oligomerisation feed stock was a Pacol product cut compressing of $C_{10}$ to $C_{14}$ olefin-paraffin mixture having 15% olefins. Some typical results are described in Table-1 & 2.

EXAMPLE-4

The reaction was carried out as described for example 1, and using the identical catalyst composition, except that the oligomerisation feed stock was a cracked refinery stream cut, having boiling range of 180–220°C., comprising of linear $C_{10}$ to $C_{14}$ hydrocarbons, having 32% olefins, 44% paraffins, 20% naphthenes and 4% aromatics . Some typical results are described in Table-1 & 2.

EXAMPLE-5

The reaction was carried out as described for example 1, and using the identical catalyst composition, except that the oligomerisation feed stock was a cracked refinery stream cut, processed through the step of urea adduction, having boiling range of 180–220° C., comprising of linear $C_{10}$ to $C_{14}$ hydrocarbons, having 29% olefins, 68% paraffins and 3% aromatics. Some typical results are described in Table-1 & 2.

TABLE 1

PERFORMANCE EVALUATION OF SYNTHESISED OLIGOMERS

| EXAMPLE NO. | CONVERSION (%)** | KV, cSt (100° C.) | VI | POUR POINT (° C.) |
|---|---|---|---|---|
| 1 | 97 | 22.1 | 140 | −27 |
| 2 | 98 | 12.3 | 132 | −30 |
| 3 | 94 | 26.5 | 134 | −27 |
| 4 | 93 | 20.4 | 142 | −30 |
| 5 | 95 | 20.9 | 138 | −30 |

**CONVERSION BASED ON OLEFIN CONTENT

TABLE 2

IP-48 OXIDATION TEST RESULTS ON SYNTHESISED OLIGOMERS AFTER HYDROGENATION

| Example No. | Kinematic Viscosity at 100° C. | | CCR (%) | | TAN (mg KOH/g) | |
|---|---|---|---|---|---|---|
| | Before Test | After Test | Before Test | After Test | Before Test | After Test |
| 1 | 22.1 | 30.9 | 0.01 | 0.13 | 0.15 | 6.4 |
| 2 | 12.3 | 17.6 | 0.01 | 0.12 | 0.17 | 6.8 |
| 3 | 26.5 | 36.8 | 0.01 | 0.17 | 0.13 | 8.3 |
| 4 | 20.4 | 29.8 | 0.01 | 0.14 | 0.15 | 8.7 |
| 5 | 20.9 | 30.5 | 0.01 | 0.15 | 0.16 | 7.9 |

What is claimed is:

1. A process for oligomerization of olefins contained in refinery distillate streams including paraffins, naphthenes and aromatics which comprises contacting the stream with a catalyst consisting of a first constituent which is at least one aluminum halide and a second constituent which is at least one alkoxide of a transition metal of Group IVB of the Periodic Table and which has a general formula:

$M(OR)_4$, where M is selected from the group consisting of metals of Group IVB of the Periodic Table and R is one of (a) an alkyl group having from 1–12 carbon atoms or (b) an alkylaryl group having an alkyl chaim having from 1–12 carbon atoms under condition effective to produce oligomerization of the olefins.

2. A process as claimed in claim 1 wherein the at least one aluminum halide is selected from the group consisting of aluminum chloride, aluminum bromide, aluminum iodide and mixtures thereof.

3. A process as claimed in claim 1 wherein the alkylaryl group has an alkyl chaim having from 2–6 carbon atoms.

4. A process as claimed in claim 1 wherein the transition metal is titanium, and wherein the at least one alkoxide is titanium alkoxide.

5. A process as claimed in claim 1 wherein the catalyst composition has a molar ratio of aluminum to transition metal which ranges from 100:1 to 4:1.

6. A process as claimed in claim 5 wherein the catalyst composition has a molar ratio of aluminum to transition metal which ranges from 60:1 to 10:1.

* * * * *